US00PP09611P

United States Patent [19]

Meier

[11] Patent Number: Plant 9,611

[45] Date of Patent: Jul. 23, 1996

[54] 'BA 69-82 ' KENTUCKY BLUEGRASS

[75] Inventor: Virgil D. Meier, Marysville, Ohio

[73] Assignee: OMS Investments, Inc., Wilmington, Del.

[21] Appl. No.: 453,864

[22] Filed: May 30, 1995

[51] Int. Cl.[6] ..... A01H 5/12

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 7/1970 | Fuchigami et al. | Plt./90.2 |
| P.P. 3,186 | 5/1972 | Barenbrug et al. | Plt./90.2 |
| P.P. 4,336 | 11/1978 | Mayer et al. | Plt./90.2 |
| P.P. 6,280 | 9/1988 | Meier et al. | Plt./90.2 |
| P.P. 6,537 | 1/1989 | Meier et al. | Plt./90.2 |
| P.P. 6,538 | 1/1989 | Meier et al. | Plt./90.2 |
| P.P. 6,585 | 2/1989 | Meier et al. | Plt./90.2 |
| P.P. 7,831 | 3/1992 | Meier et al. | Plt./90.2 |
| P.P. 8,490 | 12/1993 | Meier et al. | Plt./90.2 |
| P.P. 9,036 | 1/1995 | Meier et al. | Plt./90.2 |
| P.P. 9,209 | 7/1995 | Meier et al. | Plt./90.2 |

*Primary Examiner*—James R. Feyrer

[57] ABSTRACT

A variety of Kentucky Bluegrass having a medium to high level of resistance to leaf spot, melting out disease, several rust diseases, dollar spot, powdery mildew and stripe smut; a desirable green color throughout the growing season; the ability to form a strong sod and a high quality dense persistent turf under a wide variety of environmental conditions; and has a medium level of seed yielding capacity.

1 Drawing Sheet

BACKGROUND OF THE INVENTION

1. Field of the Invention

The present invention relates to a new and distinct variety of Poa pratensis that has been designated Ba 69-82 Kentucky Bluegrass.

2. Description of Related Art

Kentucky bluegrasses have been disclosed in U.S. Plant Pat. No. 3,156 issued May 9, 1972; U.S. Plant Pat. No. 3,186 issued May 23, 1972; U.S. Plant Pat. No. 4,336, issued Nov. 28, 1978; U.S. Plant Pat. No. 6,280 issued Sep. 6, 1988; U.S. Plant Pat. Nos. 6,537 and 6,538, issued Jan. 17, 1989; U.S. Plant Pat. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995 and pending U.S. Plant patent application Ser. No. 08/308,699, filed Sep. 19, 1994, now U.S. Plant Pat. No. 9,209.

SUMMARY OF THE VARIETY

Ba 69-82 Kentucky Bluegrass plants are a distinct variety which can be produced and asexually propogated by rhizomes, tillers and disseminules. The plants originated from random seed that germinated in the O. M. Scott and Sons plant nursery and were allowed to grow in the nursery for a period of one year. The seed and pollen parents of the random seed are believed to come from a set of 88 plants collected from several locations throughout the U.S.

Seed of Ba 69-82 Kentucky Bluegrass was produced first at Marysville, Ohio and later at Gervais, Oreg. This seed was used to plant turf performance evaluation trials and later seed production fields. Asexual production of Ba 69-82 by propagules (tillers and rhizomes) and by disseminules (modified caryopses produced by apomixis) has consistently produced progeny plants indistinguishable from the mother plant. The apomixis level of Ba 69-82 is approximately 99% based upon examining seedling characteristics of approximately 100 to 150 seedlings from different crop years in a growth chamber.

Ba 69-82 has a number of highly desirable characteristics including a high level of resistance to Drechslera spp. that causes leaf spot, melting out and crown rot; *Laetisaria*

*fuciformis* that causes red thread; *Schlerotinia homoeocarpa* that causes dollar spot; Puccinia spp. that causes several types of rust infections; *Erysiphe graminis* that causes powdery mildew; *Leptosphaeria korrae* that causes Necrotic ring spot and *Ustilago striiformis* that causes stripe smut. Ba 69-82 has an attractive leafy turf type growth habit, moderately wide leaf blades, attractive green color which can be maintained throughout the entire growing season, good drought and heat tolerance, and good turf performance as evidenced by consistently high scores for quality, color and density.

In comparison with most commercially available varieties, Ba 69-82 produces a small seed, has a short ligule and is late maturing. Under mowed conditions, Ba 69-82 develops a moderately wide blade and high sod strength. Ba 69-82 has a medium level of seed yield potential in the bluegrass seed producing regions of the northwestern U.S.

DETAILED DESCRIPTION OF THE VARIETY

Figure 1:
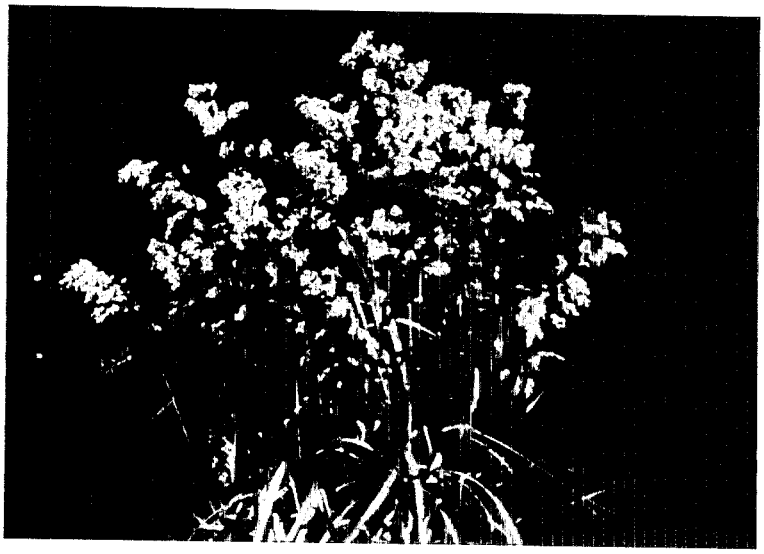
FIG. 1 is a Ba 69-82 Kentucky Bluegrass plant at anthesis.
Figure 2:
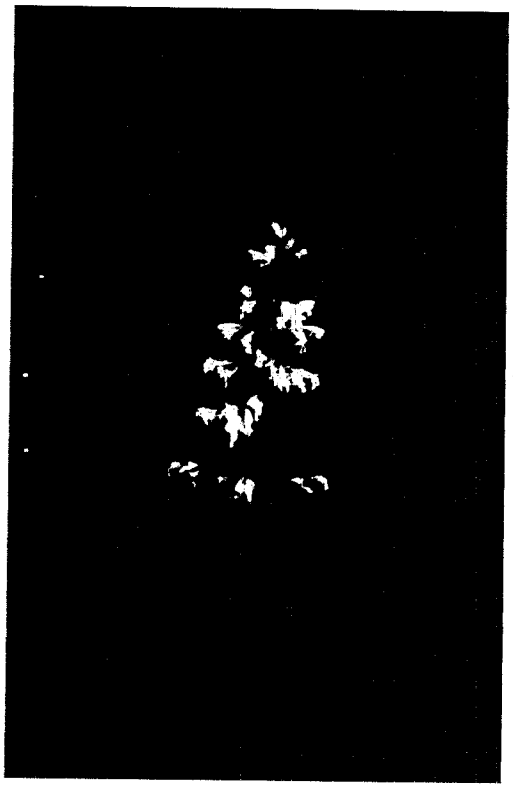
FIG. 2 is a Ba 69-82 Kentucky Bluegrass panicle at anthesis.
Figure 3:
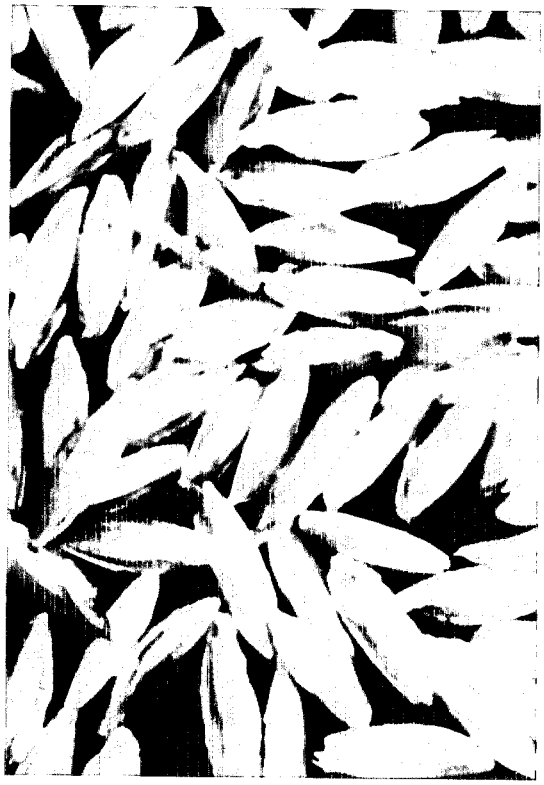
FIG. 3 is a Ba 69-82 Kentucky Bluegrass seed.

Ba 69-82 Kentucky bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60°–80° F.), culms are erect averaging 31.9 cm in length, 3.2 nodes per culm and the uppermost internode 7.2 cm in length. The peduncle averages 21.0 cm in length, and 0.595 mm in width. The vegetative leaf averages 21.9 mm in width, 0.279 mm in thickness and a ligule length of 0.14 mm. An average quantity of ligule and leaf margin hairs was observed. The flag leaf averages 4.3 cm in length, 3.2 mm in width and 0.198 mm in thickness and a ligule length of 1.0 mm. The panicle averages 67.4 mm in length, 46.6 mm in width and 8.8 whorls. The lowest whorl averages 3.3 branches and the third whorl from the bottom of the panicle 3.1 branches.

The spikelet at the tip of a branch in the lowest whorl averages 4.6 mm in length, 2.3 mm in width, 3.2 florets and 2.8 mm and 3.1 mm for the outer and inner glumes in length, respectively. A similar spikelet from the third whorl from the bottom of the panicle averages 4.7 mm in length, 2.4 mm in width, 3.3 florets and 2.9 mm and 3.2 mm for the outer and inner glumes in length, respectively. The hair content on the glumes average 2.2 and 2.2 for the outer and inner glumes on the lowest whorl, respectively, and 2.1 and 3.3 on the outer and inner glumes on the third whorl, respectively.

Ba 69-82 averaged significantly more hairs on the glumes on the third whorl than most other grasses in the study. The seed of Ba 69-82 averages 2.77 mm in length, and 0.89 mm in width, 0.68 mm in rachilla length and approximately 1,250,997 seeds per pound. The dorsal side of the lemma keel contained an average population of hairs.

Comparisons of Ba 69-82 with other Kentucky Bluegrass varieties in terms of seed dimensions and numbers per pound are shown in Tables 1 and 2 as follows:

TABLE 1

Morphological Comparison of Seed and Rachilla Measurements and Lemma Hair of Ba 69–82 and Other Kentucky Bluegrass Varieties After Conditioning.

| | Seed | | | |
|---|---|---|---|---|
| Variety | Length mm | Width mm | Rachilla mm | Lemma[1] Hair |
| Ba 69–82 | 2.77 | 0.89 | 0.68 | 4.4 |
| Ba 73–540 | 2.77 | 0.86 | 0.70 | 4.7 |
| Abbey | 2.97 | 0.89 | 0.80 | 3.8 |
| Adelphi | 2.70 | 0.84 | 0.65 | 4.4 |
| America | 2.40 | 0.68 | 0.68 | 2.8 |
| Baron | 3.08 | 0.81 | 0.71 | 5.0 |
| Bristol | 2.94 | 0.88 | 0.73 | 4.3 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Marquis | 2.97 | 0.87 | 0.83 | 4.7 |
| Midnight | 2.94 | 0.76 | 0.78 | 5.7 |
| Nassau | 3.07 | 0.86 | 0.68 | 3.4 |
| Ram I | 3.23 | 0.89 | 0.80 | 6.0 |
| Touchdown | 2.93 | 0.88 | 0.71 | 4.6 |
| Victa | 3.00 | 0.80 | 0.82 | 3.5 |
| LSD (.05) | 0.16 | 0.05 | 0.13 | 0.86 |

[1]Rating Scale: 0–9; 9 = abundant row of hairs along keel.

TABLE 2

Comparison of Seed Numbers Per Pound of Ba 69–82 and Other Kentucky Bluegrass Varieties After Conditioning

| Variety | Seeds per Pounds |
|---|---|
| Ba 69–82 | 1,250,997 |
| Ba 73–540 | 1,359,914 |
| Abbey | 1,003,037 |
| Adelphi | 1,383,976 |
| America | 1,659,824 |
| Baron | 1,051,693 |
| Bristol | 1,270,821 |
| Chateau | 1,300,105 |
| Coventry | 1,246,200 |
| Eclipse | 1,335,668 |
| Georgetown | 1,431,000 |
| Gnome | 1,017,641 |

TABLE 2-continued

Comparison of Seed Numbers Per Pound of Ba 69–82 and Other Kentucky Bluegrass Varieties After Conditioning

| Variety | Seeds per Pounds |
|---|---|
| Kelly | 921,166 |
| Marquis | 1,054,642 |
| Midnight | 1,227,000 |
| Nassau | 1,127,130 |
| Ram 1 | 1,214,000 |
| Touchdown | 1,211,000 |
| Victa | 1,038,298 |

Since environmental conditions such as soil and climate may influence morphological characteristics to some extent, comparisons of morphological characteristics of Ba 69-82 were made with other Kentucky Bluegrass varieties and the comparisons are set forth in the following Tables 3–8:

TABLE 3

Morphological Comparison of Panicles, Whorl Number and Whorl Branches of Ba 69–82 and Other Kentucky Bluegrass Varieties in the Greenhouse at Marysville, OH.

| | Panicles | | | | Number of Branches | |
|---|---|---|---|---|---|---|
| Variety | Nodding | Length mm | Width mm | Whorl Number | Lower Whorl | Third Whorl |
| Ba 69–82 | 1.5 | 67.4 | 46.6 | 8.8 | 3.3 | 3.1 |
| Ba 73–540 | 2.2 | 60.8 | 47.6 | 8.4 | 3.9 | 3.0 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| America | 2.3 | 67.7 | 51.1 | 8.8 | 3.3 | 3.5 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| Georgetown | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Marquis | 1.1 | 82.0 | 63.0 | 10.3 | 3.9 | 3.6 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Ram I | 1.3 | 67.7 | 47.0 | 7.3 | 3.0 | 3.2 |
| Touchdown | 1.1 | 73.1 | 75.0 | 7.6 | 2.1 | 2.3 |
| Victa | 1.7 | 74.9 | 58.3 | 10.0 | 4.7 | 3.5 |
| LSD (.05) | 0.68 | 7.35 | 8.62 | 0.66 | 0.72 | 0.50 |

*Rating Scale: 1–9; 9 = most nodding

TABLE 4

Morphological Comparison of Spikelets and Florets of Ba 69–82 and Other Kentucky Bluegrass Varieties in the Greenhouse at Marysville, OH.

| | Spikelet | | | | Number of Florets | |
|---|---|---|---|---|---|---|
| | Lower Whorl | | Third Whorl | | Per Spikelet | |
| Variety | Length mm | Width mm | Length mm | Width Number | Lower Whorl | Third Whorl |
| Ba 69–82 | 4.6 | 2.3 | 2.7 | 2.4 | 3.2 | 3.3 |
| Ba 73–540 | 4.3 | 2.2 | 4.3 | 2.2 | 3.4 | 3.2 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| America | 4.6 | 2.2 | 4.4 | 2.3 | 4.5 | 4.3 |

TABLE 4-continued

Morphological Comparison of Spikelets and Florets of Ba 69–82 and Other Kentucky Bluegrass Varieties in the Greenhouse at Marysville, OH.

| | Spikelet | | | | | |
|---|---|---|---|---|---|---|
| | Lower Whorl | | Third Whorl | | Number of Florets Per Spikelet | |
| Variety | Length mm | Width mm | Length mm | Width Number | Lower Whorl | Third Whorl |
| Baron | 5.4 | 2.8 | 5.4 | 3.1 | 4.0 | 4.2 |
| Bristol | 4.9 | 2.4 | 5.0 | 2.5 | 4.2 | 4.5 |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Marquis | 4.3 | 2.2 | 4.4 | 2.3 | 3.1 | 2.9 |
| Midnight | 5.3 | 2.5 | 5.5 | 2.4 | 4.4 | 4.7 |
| Nassau | 4.7 | 2.6 | 4.8 | 3.00 | 4.2 | 4.3 |
| Ram I | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| LSD (.05) | 0.41 | 0.35 | 0.38 | 0.35 | 0.58 | 0.53 |

TABLE 5

Morphological Comparison of Glumes of Ba 69–82 and Other Kentucky Bluegrass Varieties in the Greenhouse at Marysville, OH.

| | Glume Length (mm) | | | |
|---|---|---|---|---|
| | Outer | | Inner | |
| Variety | Lowest Whorl | Third Whorl | Lowest Whorl | Third Whorl |
| Ba 69–82 | 2.8 | 2.9 | 3.1 | 3.2 |
| Ba 73–540 | 2.6 | 2.7 | 3.0 | 3.0 |
| Abbey | 2.7 | 2.7 | 3.1 | 3.1 |
| Adelphi | 2.7 | 2.6 | 3.0 | 3.1 |
| America | 2.1 | 2.1 | 2.5 | 2.5 |
| Baron | 3.1 | 3.2 | 3..6 | 3.7 |
| Bristol | 2.8 | 3.0 | 3.3 | 3.4 |
| Chateau | 2.8 | 2.9 | 3.1 | 3.2 |
| Coventry | 2.7 | 2.8 | 3.1 | 3.1 |
| Eclipse | 3.0 | 3.0 | 3.4 | 3.4 |
| Georgetown | 2.8 | 2.8 | 3.1 | 3.1 |
| Gnome | 2.8 | 2.9 | 3.3 | 3.3 |
| Kelly | 3.0 | 3.1 | 3.4 | 3.5 |
| Marquis | 2.8 | 2.7 | 3.1 | 3.1 |
| Midnight | 2.6 | 2.6 | 3.0 | 3.1 |
| Nassau | 2.6 | 2.7 | 2.9 | 3.0 |
| Ram I | 2.9 | 3.0 | 3.6 | 3.5 |
| Touchdown | 3.3 | 3.3 | 3.8 | 3.8 |
| Victa | 2.8 | 2.7 | 3.1 | 3.1 |
| LSD (.05) | 0.23 | 0.22 | 0.22 | 0.23 |

| | Glume Hairs* | | | |
|---|---|---|---|---|
| | Lowest Whorl | | Third Whorl | |
| Variety | Outer | Inner | Outer | Inner |
| Ba 69–82 | 2.2 | 2.2 | 2.1 | 3.1 |
| Ba 73–540 | 2.5 | 3.0 | 2.5 | 2.5 |
| Abbey | 0.6 | 0.9 | 1.0 | 1.0 |
| Adelphi | 0.6 | 2.7 | 1.1 | 1.9 |
| America | 0.2 | 0.5 | 0.3 | 0.3 |
| Baron | 4.8 | 4.4 | 4.2 | 4.6 |
| Bristol | 1.0 | 2.2 | 0.8 | 2.2 |

TABLE 5-continued

Morphological Comparison of Glumes of Ba 69–82 and Other Kentucky Bluegrass Varieties in the Greenhouse at Marysville, OH.

| | | | | |
|---|---|---|---|---|
| Chateau | 1.5 | 2.6 | 2.0 | 1.8 |
| Coventry | 1.5 | 2.7 | 1.6 | 2.4 |
| Eclipse | 1.5 | 1.9 | 1.8 | 1.9 |
| Georgetown | 1.7 | 2.7 | 1.2 | 2.5 |
| Gnome | 1.0 | 1.9 | 1.2 | 1.6 |
| Kelly | 1.3 | 1.5 | 1.1 | 0.8 |
| Marquis | 0.9 | 1.1 | 1.7 | 1.8 |
| Midnight | 1.8 | 2.8 | 1.0 | 2.4 |
| Nassau | 2.1 | 2.6 | 4.2 | 4.4 |
| Ram I | 1.1 | 2.3 | 0.7 | 1.2 |
| Touchdown | 0.7 | 2.1 | 1.1 | 1.4 |
| Victa | 0.8 | 1.1 | 1.1 | 1.3 |
| LSD (.05) | 0.9 | 0.9 | 0.9 | 0.9 |

*Rating Scale: 0–9; 9 = most hairs

TABLE 6

Morphological comparison of Flag Leaf of Ba 69–82 and Other Kentucky Bluegrass Varieties in the Greenhouse at Marysville, OH.

| | Length | Width | Thickness | Leaf | |
|---|---|---|---|---|---|
| Variety | mm | mm | mm | Angle[1] | Curve[2] |
| Ba 69–82 | 4.3 | 3.2 | 0.198 | 1.0 | 4.9 |
| Ba 73–540 | 3.8 | 2.9 | 0.206 | 1.0 | 4.9 |
| Abbey | 3.8 | 3.4 | 0.145 | 2.7 | 4.1 |
| Adelphi | 5.7 | 3.4 | 0.178 | 5.2 | 5.0 |
| America | 4.3 | 2.6 | 0.211 | 4.6 | 5.0 |
| Baron | 7.0 | 4.2 | 0.152 | 9.2 | 4.4 |
| Bristol | 4.3 | 3.2 | 0.211 | 2.3 | 5.0 |
| Chateau | 4.0 | 2.7 | 0.193 | 3.4 | 2.0 |
| Coventry | 3.7 | 3.0 | 0.140 | 0.7 | 4.3 |
| Eclipse | 3.9 | 3.2 | 0.193 | 8.7 | 5.0 |
| Georgetown | 5.7 | 2.8 | 0.221 | 1.9 | 5.0 |
| Gnome | 4.5 | 3.5 | 0.185 | 4.3 | 5.0 |
| Kelly | 4.8 | 4.1 | 0.178 | 3.1 | 4.4 |
| Marquis | 5.5 | 3.6 | 0.241 | 2.7 | 4.6 |
| Midnight | 3.8 | 2.6 | 0.189 | 1.1 | 5.0 |
| Nassau | 6.0 | 3.7 | 0.191 | 5.9 | 4.7 |
| Ram I | 3.4 | 3.1 | 0.191 | 1.0 | 4.8 |
| Touchdown | 4.1 | 2.7 | 0.163 | 3.4 | 4.1 |
| Victa | 3.9 | 3.7 | 0.267 | 2.1 | 4.6 |
| LSD (.05) | 1.0 | 0.4 | 0.02 | 2.5 | 2.4 |

| | | Hairs[3] | | |
|---|---|---|---|---|
| Variety | Ligule mm | Leaf Margin | Ligule | Sheath[4] Color |
| Ba 69–82 | 1.0 | 0.1 | 2.5 | 1.7 |
| Ba 73–540 | 0.8 | 0.4 | 2.3 | 2.0 |
| Abbey | 1.3 | 0.8 | 1.6 | 0.2 |
| Adelphi | 1.1 | 1.8 | 1.6 | 0.4 |
| America | 0.6 | 0.4 | 0.7 | 1.9 |
| Baron | 1.2 | 1.0 | 3.8 | 2.6 |
| Bristol | 0.6 | 0.4 | 1.9 | 2.0 |
| Chateau | 0.9 | 1.1 | 3.1 | 0.3 |
| Coventry | 0.9 | 0.8 | 1.7 | 2.0 |
| Eclipse | 1.1 | 1.0 | 1.0 | 0.2 |
| Georgetown | 0.6 | 0.6 | 2.0 | 2.0 |
| Gnome | 0.8 | 0.9 | 3.2 | 1.5 |
| Kelly | 1.5 | 1.1 | 2.5 | 2.2 |
| Marquis | 0.8 | 0.5 | 3.8 | 1.5 |
| Midnight | 0.4 | 0.4 | 0.3 | 2.0 |
| Nassau | 1.1 | 2.6 | 2.4 | 0.8 |
| Ram I | 0.7 | 0.5 | 1.3 | 2.0 |
| Touchdown | 1.1 | 1.0 | 1.0 | 7.7 |
| Victa | 1.3 | 1.0 | 0.8 | 0.5 |
| LSD (.05) | 0.17 | 0.47 | 0.7 | 0.76 |

[1]Degrees from the stem

TABLE 6-continued

Morphological comparison of Flag Leaf of Ba 69–82 and Other Kentucky Bluegrass Varieties in the Greenhouse at Marysville, OH.

[2]Rating Scale: 1–9; 1 = curves up; 5 = no curve; 9 = curves down
[3]Rating Scale: 0–9; 0 = none; 9 = many
[4]Rating Scale: 0–9; 0 = no color; dark purple

TABLE 7

Morphological Comparison of Peduncles, Culms, Node Numbers Per Culm and Internode Lenght of Ba 69–82 and Other Kentucky Bluegrass Varieties in the Greenhouse at Marysville, OH.

| Variety | Peduncle Length cm | Peduncle Width mm | Culm Length cm | Nodes Per Culm | Top Internode Length cm |
|---|---|---|---|---|---|
| Ba 69–82 | 21.0 | 0.595 | 31.9 | 3.2 | 7.2 |
| Ba 73–540 | 17.9 | 0.612 | 28.0 | 3.1 | 7.7 |
| Abbey | 23.2 | 0.655 | 41.3 | 4.1 | 11.0 |
| Adelphi | 24.5 | 0.665 | 40.0 | 4.0 | 10.4 |
| America | 16.2 | 0.622 | 31.8 | 3.1 | 11.0 |
| Baron | 34.0 | 0.701 | 52.8 | 4.2 | 12.8 |
| Bristol | 22.9 | 0.734 | 43.5 | 4.0 | 12.6 |
| Chateau | 20.7 | 0.607 | 38.9 | 4.4 | 9.9 |
| Coventry | 19.6 | 0.487 | 34.7 | 4.5 | 7.9 |
| Eclipse | 23.7 | 0.658 | 39.2 | 4.9 | 9.9 |
| Georgetown | 21.7 | 0.683 | 37.5 | 3.2 | 11.1 |
| Gnome | 19.4 | 0.836 | 35.3 | 3.1 | 9.2 |
| Kelly | 29.4 | 0.752 | 46.6 | 3.6 | 11.8 |
| Marquis | 27.1 | 0.831 | 34.1 | 3.4 | 7.8 |
| Midnight | 20.5 | 0.722 | 29.5 | 2.8 | 7.6 |
| Nassau | 25.0 | 0.663 | 36.0 | 3.9 | 7.4 |
| Ram I | 22.2 | 0.694 | 30.5 | 2.5 | 6.6 |
| Touchdown | 23.6 | 0.519 | 38.0 | 4.0 | 8.4 |
| Victa | 21.2 | 0.808 | 37.9 | 3.7 | 10.3 |
| LSD (.05) | 3.2 | 0.08 | 3.3 | 0.4 | 1.9 |

TABLE 8

Morphological Comparison of Vegetative Leaves of Ba 69–82 and Other Bluegrass Varieties in the Greenhouse at Marysville, Ohio.

| Variety | Length mm | Width mm | Thickness mm | Leaf Angle[1] | Leaf Curve[2] |
|---|---|---|---|---|---|
| Ba 69–82 | 21.9 | 3.5 | 0.279 | 51.7 | 8.3 |
| Ba 73–540 | 18.1 | 3.5 | 0.300 | 53.0 | 6.2 |
| Abbey | 20.7 | 3.6 | 0.277 | 51.3 | 7.4 |
| Adelphi | 19.4 | 3.7 | 0.279 | 67.0 | 4.6 |
| America | 21.4 | 3.1 | 0.325 | 66.0 | 6.4 |
| Baron | 18.2 | 4.3 | 0.290 | 35.0 | 4.4 |
| Bristol | 18.2 | 3.7 | 0.320 | 65.5 | 6.9 |
| Chateau | 23.1 | 3.3 | 0.328 | 39.7 | 5.4 |
| Coventry | 23.4 | 3.6 | 0.249 | 63.0 | 7.3 |
| Eclipse | 20.3 | 4.4 | 0.302 | 65.5 | 5.4 |
| Georgetown | 19.5 | 3.6 | 0.287 | 56.7 | 5.8 |
| Gnome | 18.2 | 2.9 | 0.290 | 43.2 | 6.6 |
| Kelly | 22.8 | 3.9 | 0.300 | 55.5 | 7.0 |
| Marquis | 19.7 | 3.7 | 0.376 | 46.8 | 7.8 |
| Midnight | 19.5 | 3.5 | 0.310 | 63.3 | 5.0 |
| Nassau | 16.3 | 3.7 | 0.292 | 63.2 | 4.9 |
| Ram I | 19.1 | 3.6 | 0.271 | 70.8 | 6.5 |
| Touchdown | 16.7 | 3.7 | 0.243 | 51.3 | 4.0 |
| Victa | 21.5 | 3.6 | 0.360 | 56.3 | 6.7 |
| LSD (.05) | 3.5 | 0.43 | 0.04 | 15.9 | 1.5 |

TABLE 8-continued

Morphological Comparison of Vegetative Leaves of Ba 69–82 and Other Bluegrass Varieties in the Greenhouse at Marysville, Ohio.

| Variety | Hairs[3] Ligule mm | Hairs[3] Ligule | Hairs[3] Leaf Margin | Leaf Roughness[4] | Sheath Color[5] |
|---|---|---|---|---|---|
| Ba 69–82 | 0.14 | 2.7 | 1.4 | 8.1 | 1.7 |
| Ba 73–540 | 0.14 | 2.0 | 1.6 | 8.3 | 1.9 |
| Abbey | 0.32 | 4.4 | 2.8 | 7.7 | 0.0 |
| Adelphi | 0.34 | 2.6 | 3.4 | 8.8 | 0.0 |
| America | 0.12 | 1.7 | 2.1 | 8.4 | 2.0 |
| Baron | 0.33 | 4.6 | 3.6 | 7.4 | 0.4 |
| Bristol | 0.12 | 2.6 | 3.0 | 8.9 | 2.0 |
| Chateau | 0.22 | 3.3 | 3.1 | 7.8 | 0.5 |
| Coventry | 0.32 | 3.1 | 2.4 | 8.1 | 0.3 |
| Eclipse | 0.38 | 2.8 | 2.6 | 9.0 | 0.2 |
| Georgetown | 0.14 | 2.5 | 2.4 | 8.5 | 2.0 |
| Gnome | 0.23 | 1.6 | 0.8 | 7.5 | 1.4 |
| Kelly | 0.34 | 4.6 | 2.4 | 8.8 | 0.0 |
| Marquis | 0.21 | 3.6 | 1.1 | 6.8 | 1.1 |
| Midnight | 0.10 | 1.3 | 1.6 | 7.7 | 2.0 |
| Nassau | 0.34 | 2.5 | 3.3 | 8.5 | 1.4 |
| Ram I | 0.09 | 1.8 | 2.0 | 7.7 | 2.0 |
| Touchdown | 0.29 | 1.4 | 1.3 | 7.9 | 8.0 |
| Victa | 0.26 | 2.3 | 1.7 | 7.9 | 0.1 |
| LSD (.05) | 0.04 | 0.79 | 0.70 | 089 | 0.57 |

[1]Degrees from stem
[2]Rating Scale: 1–9; 1 = curves up; 5 = no curve; 9 = curves down
[3]Rating Scale: 0–9; 1 = none; 9 = many
[4]Rating Scale: 1–9; 1 = rough; 9 = smooth
[5]Rating Scale: 0–9; 0 = no color; 9 = dark purple color Ba 69-82 has performed well throughout the U.S. and Canada as exhibited by high turf quality ratings in a number of locations across the U.S. in comparison to other Kentucky Bluegrass varieties. In addition, it has a pleasant medium green color which can be maintained throughout the growing season and good winter color. It demonstrates early spring greening and good spring density.

With regard to a comparative analysis conducted for purposes of determining color of Ba 69-82 plants relative to other Kentucky Bluegrass varieties, readings were taken of the vegetative color of Ba 69-82 during mid-May while the turf was actively growing with adequate nutrient and water availability. The readings were taken in full sun with several actively growing leaves being compared, one at a time, utilizing color chips from the Munsell Book of Color as a reference. On this basis, the color of Ba 69-82 was determined to be 5 GY 4/4. During the same time period, the color of similar leaves of other Kentucky Bluegrass varieties were determined by the same procedure to be as follows: Ba 73-381-5 GY 4/4; Ba 73-366-5 GY 4/4; Ba 73-540-5 GY 4/4; Abbey - 5GY 3/4; and Coventry-5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Comparisons of Ba 69-82 with other Kentucky Bluegrass varieties for quality, genetic color, winter color and spring greening are set forth hereinafter in Tables 9–12;

TABLE 9

A Comparison of Quality of Ba 69–82 and Other Kentucky Bluegrass Varieties in Four Annual Tests (A–D) Conducted at Forty Turfgrass Locations in the U.S. and Canada

| | TESTS (Annual/Means) | | | |
|---|---|---|---|---|
| Variety | A | B | C | D |
| Ba 69–82 | 5.7 | 5.7 | 6.1 | 5.8 |
| Ba 73–540 | 5.8 | 5.9 | 6.0 | 5.8 |
| Abbey | 5.6 | 5.7 | 5.9 | 5.7 |
| Able 1 | 5.7 | 5.7 | 6.0 | 6.1 |
| Amazon | 5.4 | 5.5 | 5.5 | 5.5 |
| America | 5.8 | 5.9 | 6.1 | 6.2 |
| A-34 | 5.6 | 5.9 | 6.0 | 6.1 |
| Baron | 5.8 | 5.6 | 5.9 | 5.8 |
| Bristol | 5.7 | 6.0 | 6.1 | 6.0 |
| Chateau | 6.0 | 5.8 | 6.0 | 6.0 |
| Classic | 5.9 | 5.8 | 6.0 | 5.9 |
| Coventry | 5.8 | 5.8 | 5.9 | 5.8 |
| Eclipse | 5.6 | 5.9 | 6.2 | 6.3 |
| Estate | 5.9 | 5.9 | 5.9 | 5.8 |
| Georgetown | 5.8 | 5.6 | 5.8 | 5.8 |
| Glade | 5.7 | 5.8 | 6.1 | 6.1 |
| Gnome | 5.5 | 5.3 | 5.6 | 5.5 |
| Haga | 5.8 | 5.8 | 5.8 | 5.9 |
| Kelly | 5.6 | 5.7 | 5.9 | 5.8 |
| Kenblue | 5.0 | 4.7 | 5.0 | 5.2 |
| Marquis | 5.3 | 5.6 | 5.7 | 5.7 |
| Merion | 5.4 | 5.4 | 5.7 | 5.6 |
| Merit | 5.6 | 5.6 | 5.9 | 5.8 |
| Midnight | 6.1 | 6.3 | 6.4 | 6.3 |
| Monopoly | 5.5 | 5.5 | 5.9 | 5.9 |
| Nassau | 5.6 | 5.7 | 5.8 | 5.5 |
| Ram I | 5.7 | 5.6 | 5.9 | 5.8 |
| Victa | 5.8 | 5.7 | 5.8 | 5.8 |
| LSD (.05) | 0.2 | 0.2 | 0.2 | 0.2 |

Rating Scale: 1–9; 9 = ideal turf
*Not all forty locations reported data each year.

TABLE 10

A Comparison of Genetic Color of Ba 69–82 and Other Kentucky Bluegrass Varieties at 15 Locations in the U.S. and Canada

| | TESTS (Annual Means) | | | |
|---|---|---|---|---|
| Variety | A | B | C | D |
| Ba 69–82 | 6.8 | 6.1 | 6.4 | 6.3 |
| Ba 73–540 | 6.5 | 6.2 | 6.3 | 6.5 |
| Abbey | 6.8 | 6.2 | 6.7 | 6.6 |
| Able I | 7.1 | 6.8 | 6.7 | 6.9 |
| Amazon | 6.2 | 6.9 | 7.0 | 6.5 |
| America | 6.8 | 6.6 | 7.0 | 6.6 |
| A-34 | 5.7 | 5.6 | 5.7 | 5.7 |
| Baron | 6.8 | 6.5 | 6.9 | 6.8 |
| Bristol | 7.3 | 7.1 | 6.6 | 6.6 |
| Chateau | 6.5 | 6.0 | 6.2 | 6.5 |
| Classic | 5.8 | 5.6 | 6.3 | 5.9 |
| Coventry | 6.5 | 6.0 | 6.5 | 6.6 |
| Eclipse | 7.7 | 6.7 | 6.5 | 6.6 |
| Estate | 6.7 | 5.9 | 6.3 | 6.6 |
| Georgetown | 6.1 | 5.7 | 5.9 | 6.7 |
| Glade | 7.4 | 7.0 | 6.7 | 6.9 |
| Gnome | 6.4 | 6.5 | 6.8 | 6.7 |
| Haga | 5.8 | 5.5 | 6.1 | 5.8 |
| Kelly | 6.7 | 6.5 | 6.9 | 6.5 |
| Kenblue | 5.2 | 5.2 | 5.5 | 6.0 |
| Marquis | 7.2 | 6.6 | 6.8 | 6.5 |
| Merion | 6.4 | 5.6 | 6.0 | 6.5 |
| Merit | 6.7 | 6.4 | 6.5 | 6.1 |
| Midnight | 8.0 | 7.9 | 7.5 | 7.7 |
| Monopoly | 5.3 | 5.5 | 5.5 | 5.3 |
| Nassau | 7.1 | 6.7 | 6.9 | 6.8 |
| Ram I | 6.9 | 6.6 | 6.9 | 6.6 |

TABLE 10-continued

A Comparison of Genetic Color of Ba 69–82 and Other Kentucky Bluegrass Varieties at 15 Locations in the U.S. and Canada

| | TESTS (Annual Means) | | | |
|---|---|---|---|---|
| Variety | A | B | C | D |
| Victa | 6.7 | 6.3 | 6.7 | 6.5 |
| LSD (.05) | 0.4 | 0.4 | 0.4 | 0.4 |

Rating Scale; 1–9:9 = dark green

TABLE 11

A Comparison of Spring Greenup for Ba 69–82 and Other Kentucky Bluegrass Varieties at Five Locations* in the U.S. and Canada

| Variety | Annual Means |
|---|---|
| Ba 69–82 | 4.8 |
| Ba 73–540 | 4.6 |
| Abbey | 4.2 |
| Able I | 3.7 |
| Amazon | 3.7 |
| America | 3.9 |
| A-34 | 5.2 |
| Baron | 4.2 |
| Bristol | 5.0 |
| Chateau | 4.9 |
| Classic | 4.5 |
| Coventry | 4.6 |
| Eclipse | 4.5 |
| Estate | 4.6 |
| Georgetown | 4.2 |
| Glade | 4.9 |
| Gnome | 3.9 |
| Haga | 4.5 |
| Kelly | 4.0 |
| Kenblue | 5.1 |
| Marquis | 4.0 |
| Merion | 4.3 |
| Merit | 3.9 |
| Midnight | 3.9 |
| Monopoly | 4.1 |
| Nassau | 5.2 |
| Ram I | 4.3 |
| Victa | 4.3 |
| LSD (.05) | 0.7 |

Rating Scale: 1–9:9 = completely green.
*Locations: Agassiz, British Columbia; Post Fall, ID; West Lafayette, In; Columbus, OH; Kingston, RI.

TABLE 12

A Comparison of Winter Color of Ba 69–82 and Other Kentucky Bluegrass Varieties in the U.S. and Canada

| | Winter Color | |
|---|---|---|
| Variety | Wichita, Kansas | Agassiz British Columbia |
| Ba 69–82 | 5.0 | 5.0 |
| Ba 73–540 | 5.0 | 5.0 |
| Abbey | 3.0 | 4.7 |
| Able I | 5.7 | 4.0 |
| Amazon | 4.0 | 4.0 |
| America | 4.7 | 4.0 |
| A-34 | 4.7 | 4.3 |
| Baron | 3.3 | 4.7 |
| Bristol | 5.7 | 5.0 |
| Chateau | 5.0 | 5.0 |
| Classic | 5.0 | 4.0 |
| Coventry | 5.0 | 5.0 |

TABLE 12-continued

A Comparison of Winter Color of Ba 69–82 and Other Kentucky Bluegrass Varieties in the U.S. and Canada

| Variety | Winter Color: Wichita, Kansas | Winter Color: Agassiz British Columbia |
|---|---|---|
| Eclipse | 4.0 | 4.3 |
| Estate | 4.3 | 5.0 |
| Georgetown | 5.3 | 4.0 |
| Glade | 3.3 | 4.3 |
| Gnome | 2.7 | 4.3 |
| Haga | 5.0 | 4.0 |
| Kelly | 3.7 | 4.7 |
| Kenblue | 3.0 | 3.0 |
| Marquis | 3.3 | 4.3 |
| Merion | 3.0 | 4.0 |
| Merit | 3.3 | 5.0 |
| Midnight | 4.3 | 4.7 |
| Monopoly | 3.7 | 4.7 |
| Nassau | 5.7 | 5.0 |
| Ram I | 5.0 | 4.7 |
| Victa | 3.7 | 5.0 |
| LSD (.05) | 1.0 | 0.6 |

Rating Scale: 1–9; 9 = complete color retention.

Further comparisons of Ba 69-82 with other Kentucky Bluegrass varieties for leaf texture and spring, summer and fall density are given in Tables 13–16 as follows:

TABLE 13

A Comparison of Leaf Texture of Ba 69–82 and Other Kentucky Bluegrass Varieties in Two Annual Tests (A–B) Conducted at Eight Locations in the U.S. and Canada*

| Variety | TESTS (Annual Means) A | TESTS (Annual Means) B |
|---|---|---|
| Ba 69–82 | 5.7 | 5.8 |
| Ba 73–540 | 5.8 | 5.6 |
| Abbey | 6.3 | 6.3 |
| Able I | 7.1 | 7.3 |
| Amazon | 7.5 | 7.2 |
| America | 7.1 | 7.2 |
| A-34 | 6.4 | 6.9 |
| Baron | 6.8 | 6.1 |
| Barzan | 6.1 | 6.7 |
| Bristol | 6.7 | 6.3 |
| Chateau | 6.1 | 6.0 |
| Classic | 6.6 | 7.0 |
| Coventry | 5.9 | 5.7 |
| Eclipse | 6.4 | 6.5 |
| Estate | 6.3 | 5.9 |
| Georgetown | 6.8 | 6.8 |
| Glade | 6.8 | 6.7 |
| Gnome | 6.1 | 6.2 |
| Haga | 6.7 | 7.1 |
| Kelly | 6.4 | 5.7 |
| Kenblue | 7.8 | 7.3 |
| Marquis | 6.1 | 5.7 |
| Merion | 6.7 | 6.8 |
| Merit | 6.3 | 6.1 |
| Midnight | 7.3 | 6.7 |
| Monopoly | 7.1 | 6.8 |
| Nassau | 6.6 | 6.5 |
| Ram I | 7.3 | 7.1 |
| Victa | 6.3 | 6.0 |
| LSD (.05) | 0.5 | 0.5 |

Rating Scale: 1–9; 9 = very fine
*Locations Test A: West Lafayette, In.; Columbia, Mo.; Farmington, NM; Columbus, OH.; Brookings, SD; Puyallup, WA.
Locations Test B: Agassiz, British Columbia; Post Falls, ID.; Columbus, OH.; Brookings, SD,; Puyallup, WA.

TABLE 14

A Comparison of Spring Density for Ba 69–82 and Other Kentucky Bluegrass Varieties in Two Annual Tests (A–B) Conducted at Five Locations* in the U.S. and Canada

| Variety | TESTS (Annual Means) A | TESTS (Annual Means) B |
|---|---|---|
| Ba 69–82 | 6.7 | 7.1 |
| Ba 73–540 | 6.5 | 7.6 |
| Abbey | 5.8 | 6.8 |
| Able I | 5.8 | 7.4 |
| Amazon | 6.7 | 6.7 |
| America | 6.2 | 7.1 |
| A-34 | 5.7 | 7.3 |
| Baron | 6.3 | 6.8 |
| Bristol | 5.3 | 6.9 |
| Chateau | 6.7 | 7.3 |
| Classic | 5.5 | 7.2 |
| Coventry | 6.5 | 7.1 |
| Eclipse | 5.5 | 7.1 |
| Estate | 6.3 | 7.2 |
| Georgetown | 5.5 | 6.9 |
| Glade | 6.8 | 7.3 |
| Gnome | 6.0 | 6.3 |
| Haga | 5.5 | 7.3 |
| Kelly | 6.3 | 6.7 |
| Kenblue | 6.2 | 6.0 |
| Marquis | 6.0 | 6.6 |
| Merion | 6.3 | 7.3 |
| Merit | 5.8 | 6.7 |
| Midnight | 6.7 | 7.4 |
| Monopoly | 6.2 | 7.0 |
| Nassau | 6.2 | 6.6 |
| Ram I | 7.0 | 6.4 |
| Victa | 5.8 | 6.8 |
| LSD (.05) | 0.8 | 0.7 |

Rating Scale: 1–9; 9 = maximum density
*Locations Test A: Winnipeg, Manitoba; Columbus, OH.
Locations Test B: Columbia, Mo; University Park, Pa.; Brookings, SD.

TABLE 15

A Comparison of Summer Density of Ba 69–82 and Other Kentucky Bluegrass Varieties in Two Annual Tests (A–B) Conducted at Four Locations in the U.S. and Canada*

| Variety | TESTS (Annual Means) A | TESTS (Annual Means) B |
|---|---|---|
| Ba 69–82 | 6.8 | 8.2 |
| Ba 73–540 | 6.7 | 8.2 |
| Abbey | 7.1 | 8.0 |
| Able I | 6.8 | 7.8 |
| Amazon | 6.8 | 8.2 |
| America | 6.8 | 7.7 |
| A-34 | 6.8 | 7.8 |
| Baron | 6.3 | 7.7 |
| Bristol | 6.4 | 7.8 |
| Chateau | 7.3 | 8.3 |
| Classic | 6.3 | 8.0 |
| Coventry | 6.8 | 8.2 |
| Eclipse | 6.3 | 7.7 |
| Estate | 6.6 | 8.2 |
| Georgetown | 5.9 | 7.3 |
| Glade | 6.2 | 8.2 |
| Gnome | 6.3 | 7.3 |
| Haga | 6.3 | 7.7 |
| Kelly | 6.4 | 7.7 |
| Kenblue | 6.1 | 7.2 |
| Marquis | 6.3 | 7.0 |
| Merion | 6.4 | 7.8 |
| Merit | 6.3 | 7.8 |
| Midnight | 6.5 | 7.8 |
| Monopoly | 5.8 | 7.7 |
| Nassau | 6.1 | 7.0 |

TABLE 15-continued

A Comparison of Summer Density of Ba 69–82 and Other Kentucky Bluegrass Varieties in Two Annual Tests (A–B) Conducted at Four Locations in the U.S. and Canada*

| Variety | TESTS (Annual Means) A | B |
|---|---|---|
| Ram I | 6.7 | 7.8 |
| Victa | 6.2 | 8.0 |
| LSD (.05) | 0.8 | 0.7 |

Rating Scale: 1–9; 9 = maximum density
*Locations Test A: Winnipeg, Manitoba; Columbus, OH.
Locations Test B: Columbia, Mo.; Brookings, SD.

TABLE 16

A Comparison of Fall Density Ba 69–82 and Other Kentucky Bluegrass Varieties in Two Annual Tests (A–B) Conducted at Five Locations in the U.S. and Canada*

| Variety | TESTS (Annual Means) A | B |
|---|---|---|
| Ba 69–82 | 8.0 | 7.5 |
| Ba 73–540 | 8.7 | 7.8 |
| Abbey | 7.0 | 7.2 |
| Able I | 8.2 | 7.4 |
| Amazon | 9.0 | 7.8 |
| America | 8.7 | 7.5 |
| A-34 | 8.2 | 7.9 |
| Baron | 8.0 | 7.0 |
| Bristol | 7.8 | 7.5 |
| Chateau | 8.2 | 7.5 |
| Classic | 8.2 | 7.5 |
| Coventry | 9.0 | 7.3 |
| Eclipse | 8.0 | 7.5 |
| Estate | 8.0 | 7.4 |
| Georgetown | 7.3 | 7.1 |
| Glade | 7.8 | 7.6 |
| Gnome | 7.7 | 7.1 |
| Haga | 8.3 | 7.5 |
| Kelly | 7.2 | 7.8 |
| Kenblue | 8.3 | 7.5 |
| Marquis | 6.2 | 6.8 |
| Merion | 7.3 | 7.3 |
| Merit | 7.2 | 7.0 |
| Midnight | 8.3 | 8.1 |
| Monopoly | 7.5 | 7.1 |
| Nassau | 6.5 | 7.3 |
| Parade | 8.7 | 7.5 |
| Ram I | 9.0 | 7.6 |
| Victa | 7.8 | 7.1 |
| LSD (.05) | 0.5 | 0.6 |

Rating Scale: 1–9:9 = maximum density
*Locations Test A: Winnipeg, Monitoba; Brookings, SD.
Locations Test B: Post Falls, ID.; Winnipeg, Manitoba; Columbia, Mo.; Columbus, OH.

Turf diseases are one of the major causes of inconsistent and poor turf performance among locations and years. Ba 69-82 has been found to have a high level of resistance to leaf spot, melting out and crown rot caused by *Drechslera poae* (formerly called *Helminthosporium vagans*), a medium to high level of resistance to several rust diseases caused by Puccinia spp., dollarspot caused by *Sclerotina homeocarpa,* red thread caused by *Laetisaria fuciformis* (formerly called *Corticium fuciforme*), necrotic ring spot caused by *Leptosphaeria korrae,* stripe smut caused by *Ustilago striiformis,* and powdery mildew caused by *Erysinhe graminis.*

Comparisons of disease incidence in Ba 69-82 as compared with other Kentucky Bluegrass varieties in regard to leaf spot, melting out, rusts, dollarspot, red thread, stripe smut, necrotic ring spot and powdery mildew are presented in Tables 17–27. Additional comparisons are presented in Tables 28–31 for drought stress, sod strength and seed yields.

TABLE 17

A Comparison of Leaf Spot Disease Incidence in Ba 69–82 and Other Kentucky Bluegrass Varieties in Two Annual Tests Conducted at Five Locations in the U.S. and Canada*

| Variety | TEST (Annual Means) A | B |
|---|---|---|
| Ba 69–82 | 7.2 | 6.2 |
| Ba 73–540 | 5.9 | 5.7 |
| Abbey | 4.6 | 5.8 |
| Able I | 6.8 | 5.7 |
| Amazon | 5.2 | 5.8 |
| America | 5.7 | 6.5 |
| A-34 | 6.3 | 5.7 |
| Baron | 6.0 | 6.5 |
| Bristol | 7.9 | 6.5 |
| Chateau | 6.4 | 6.2 |
| Classic | 6.2 | 6.0 |
| Coventry | 5.0 | 6.2 |
| Eclipse | 7.4 | 7.0 |
| Estate | 6.8 | 5.8 |
| Georgetown | 6.7 | 6.5 |
| Glade | 7.4 | 5.8 |
| Gnome | 6.0 | 6.3 |
| Haga | 6.7 | 6.0 |
| Kelly | 5.1 | 6.2 |
| Kenblue | 4.8 | 2.0 |
| Marquis | 6.4 | 6.2 |
| Merion | 6.2 | 6.3 |
| Merit | 5.6 | 6.5 |
| Midnight | 7.2 | 6.2 |
| Monopoly | 5.6 | 6.7 |
| Nassau | 6.6 | 6.2 |
| Ram I | 4.9 | 5.0 |
| Victa | 6.0 | 6.2 |
| LSD (.05) | 1.0 | 0.9 |

Rating Scale: 1–9; 9 = no disease
*Locations Test A: Post Falls, ID.; Hubbard, OR.; Remington, VA.
Locations Test B: Beltsville, MD.; Blacksburg, VA.

TABLE 18

A Comparison of Leaf Spot Disease Incidence in Ba 69–82 and Other Kentucky Bluegrass Varieties in Three Annual Tests (A–C) Conducted at Marysville, OH

| Variety | % Leaf Spot Tests A | B | C |
|---|---|---|---|
| Ba 69–82 | 4.3 | 1.0 | 16.7 |
| Adelphi | 17.7 | 2.3 | 11.7 |
| Bristol | 5.2 | 1.0 | 5.0 |
| Marquis | 5.2 | 1.0 | 8.3 |
| Parade | 7.7 | 13.3 | 16.7 |
| Park | 62.5 | 76.7 | 90.0 |
| Vantage | 33.3 | 7.0 | 25.0 |
| Victa | 9.2 | 1.0 | 10.7 |

TABLE 18-continued

A Comparison of Leaf Spot Disease Incidence in Ba 69–82 and Other Kentucky Bluegrass Varieties in Three Annual Tests (A–C) Conducted at Marysville, OH

| | % Leaf Spot Tests | | |
|---|---|---|---|
| Variety | A | B | C |
| LSD (.05) | | 3.1 | 15.7 |

TABLE 19

A Comparison of Leaf Spot Disease Incidence in Ba 69–82 and Other Kentucky Bluegrass Varieties in Two Annual Tests (A–B) Conducted at Gervais, Oregon

| | % Leaf Spot Tests | |
|---|---|---|
| Variety | A | B |
| Ba 69–82 | 10.0 | 16.7 |
| Adelphi | 70.0 | 73.3 |
| America | 53.3 | 36.7 |
| Bristol | 5.0 | 10.0 |
| Glade | 21.7 | 36.7 |
| Kenblue | 88.3 | 66.7 |
| Marquis | 83.3 | 88.3 |
| Merit | 80.0 | 83.3 |
| Newport | 50.0 | 60.1 |
| Victa | 80.0 | 78.3 |
| LSD (.05) | 16.0 | 26.0 |

TABLE 20

A Comparison of Leaf Spot Disease Incidence in Ba 69–82 and Other Kentucky Bluegrass Varieties at Prince Fredrick, Maryland

| Variety | % Leaf Spot |
|---|---|
| Ba 69–82 | 12.5 |
| Fylking | 10.0 |
| Kenblue | 60.0 |
| Merion | 15.0 |
| Nugget | 10.0 |
| Newport | 40.0 |
| Vantage | 20.0 |
| Victa | 27.5 |
| LSD (.05) | 23 |

TABLE 21

A Comparison of Melting Out Disease Incidence in Ba 69–82 and Other Kentucky Bluegrass Varieties at Three Locations*

| | Melting Out | |
|---|---|---|
| Variety | Spring | Fall |
| Ba 69–82 | 5.0 | 9.0 |
| Ba 73–540 | 5.2 | 8.7 |
| Abbey | 3.7 | 8.0 |
| Able I | 4.5 | 9.0 |
| Amazon | 4.2 | 7.0 |
| America | 5.2 | 8.7 |
| A-34 | 4.8 | 8.7 |
| Baron | 4.3 | 8.3 |
| Bristol | 5.7 | 9.0 |
| Chateau | 5.5 | 9.0 |
| Classic | 6.2 | 8.7 |
| Coventry | 4.3 | 9.0 |
| Eclipse | 5.0 | 7.0 |
| Estate | 5.3 | 9.0 |
| Georgetown | 5.8 | 9.0 |
| Glade | 4.5 | 8.0 |

TABLE 21-continued

A Comparison of Melting Out Disease Incidence in Ba 69–82 and Other Kentucky Bluegrass Varieties at Three Locations*

| | Melting Out | |
|---|---|---|
| Variety | Spring | Fall |
| Gnome | 4.5 | 8.7 |
| Haga | 6.2 | 9.0 |
| Kelly | 3.8 | 8.3 |
| Kenblue | 3.7 | 1.0 |
| Marquis | 4.8 | 7.7 |
| Merion | 5.0 | 9.0 |
| Merit | 4.2 | 8.3 |
| Midnight | 4.0 | 9.0 |
| Monopoly | 4.5 | 8.0 |
| Nassau | 5.0 | 9.0 |
| Ram I | 4.5 | 5.3 |
| Victa | 5.2 | 8.0 |
| LSD (.05) | 0.7 | 1.6 |

Rating Scale: 1–9; 9 = no disease
*Locations: Fall - Puyallup, Wa. Spring - Blacksburg, Va.; Blackstone, Va.

TABLE 22

A Comparison of Stripe Smut Disease Incidence in Ba 69–82 and Other Kentucky Bluegrass Varieties in 2 Tests (A–B) Conducted at Prince Fredrick, Md

| | % Stripe Smut | |
|---|---|---|
| Variety | A | B |
| Ba 69–B2 | 4.0 | 1.5 |
| Fylking | 27.5 | 40.0 |
| Kenblue | 5.0 | 2.5 |
| Merion | 37.5 | 75.0 |
| Nugget | 4.0 | 17.5 |
| Newport | 12.5 | 10.0 |
| Vantage | 12.5 | 30.0 |
| Victa | 55.0 | 50.0 |
| LSD (.05) | 30 | 22 |

TABLE 23

A Comparison of Dollar Spot Disease Incidence in Ba 69–82 and Other Kentucky Bluegrass Varieties at Columbia, MO

| Variety | Dollar Spot |
|---|---|
| Ba 69–82 | 7.7 |
| Ba 73–540 | 8.0 |
| Abbey | 7.3 |
| Able I | 7.7 |
| Amazon | 6.7 |
| America | 7.3 |
| A-34 | 7.3 |
| Baron | 7.0 |
| Bristol | 7.7 |
| Chateau | 6.7 |
| Classic | 6.3 |
| Coventry | 7.7 |
| Eclipse | 7.7 |
| Estate | 7.3 |
| Georgetown | 7.3 |
| Glade | 7.3 |
| Gnome | 8.0 |
| Haga | 7.3 |
| Kenblue | 7.3 |
| Merion | 7.3 |
| Merit | 6.7 |
| Midnight | 6.7 |
| Monopoly | 7.0 |
| Nassau | 6.7 |
| Ram I | 6.0 |

TABLE 23-continued

A Comparison of Dollar Spot Disease Incidence in Ba 69–82 and Other Kentucky Bluegrass Varieties at Columbia, MO

| Variety | Dollar Spot |
|---|---|
| Victa7.7 | |
| LSD (.05) | 1.4 |

Rating Scale: 1–9; 9 = no disease

TABLE 24

A Comparison of Powdery Mildew Disease Incidence in Ba 69–82 and Other Kentucky Bluegrass Varieties in Two Annual Tests Conducted at Two Separate Locations

| | Powdery Mildew | |
|---|---|---|
| Variety | Adelphia. N J Test | Ritzville, WA Test |
| Ba 69–82 | 5.3 | 7.0 |
| Ba 73–540 | 5.7 | 6.0 |
| Abbey | 1.0 | 3.5 |
| Able I | 6.7 | 5.7 |
| Amazon | 5.0 | 4.7 |
| America | 7.7 | 8.0 |
| A-34 | 6.7 | 5.0 |
| Baron | 1.3 | 4.0 |
| Bristol | 7.0 | 8.0 |
| Chateau | 5.3 | 5.0 |
| Classic | 2.7 | 6.7 |
| Coventry | 6.0 | 6.0 |
| Eclipse | 5.0 | 6.0 |
| Estate | 7.0 | 6.7 |
| Georgetown | 2.7 | 6.0 |
| Glade | 3.3 | 6.0 |
| Gnome | 1.0 | 3.7 |
| Haga | 3.0 | 6.3 |
| Kenblue | 5.0 | 8.0 |
| Merion | 1.0 | 5.7 |
| Merit | 1.7 | 4.6 |
| Midnight | 1.7 | 4.0 |
| Monopoly | 6.7 | 7.7 |
| Nassau | 2.3 | 5.7 |
| Ram I | 6.7 | 4.7 |
| Victa | 1.7 | 4.3 |
| LSD (.05) | 1.4 | 2.3 |

Rating Scale: 1–9; 9' = no disease

TABLE 25

A Comparison of Rust Disease Incidence in Ba 69–82 and Other Kentucky Bluegrass Varieties in Annual Testing at Various Locations in the U.S. and Canada

| | Stem Rust | | Stripe Rust Agassiz, | Crown Rust Agassiz |
|---|---|---|---|---|
| Variety | Adelphia New Jersey Test | Post Falls Idaho Test | British Columbia Test | British Columbia Test |
| Ba 69–82 | 8.3 | 8.0 | 8.0 | 9.0 |
| Ba 73–540 | 8.0 | 8.0 | 8.0 | 9.0 |
| Abbey | 6.3 | 8.3 | 6.3 | 7.0 |
| Able I | 7.0 | 8.0 | 7.3 | 8.3 |
| Amazon | 6.0 | 7.3 | 7.0 | 9.0 |
| America | 8.3 | 7.7 | 8.0 | 8.3 |
| A-34 | 8.0 | 8.0 | 7.0 | 8.3 |
| Baron | 7.3 | 8.0 | 7.0 | 8.0 |
| Bristol | 8.7 | 8.0 | 8.0 | 8.3 |
| Chateau | 8.3 | 7.3 | 7.3 | 9.0 |
| Classic | 8.7 | 8.3 | 8.0 | 9.0 |
| Coventry | 8.3 | 8.0 | 8.0 | 8.0 |

TABLE 25-continued

A Comparison of Rust Disease Incidence in Ba 69–82 and Other Kentucky Bluegrass Varieties in Annual Testing at Various Locations in the U.S. and Canada

| | Stem Rust | | Stripe Rust Agassiz, | Crown Rust Agassiz |
|---|---|---|---|---|
| Variety | Adelphia New Jersey Test | Post Falls Idaho Test | British Columbia Test | British Columbia Test |
| Eclipse | 7.7 | 8.3 | 6.3 | 9.0 |
| Estate | 7.3 | 7.7 | 8.0 | 9.0 |
| Georgetown | 9.0 | 7.7 | 7.0 | 8.7 |
| Glade | 7.7 | 8.0 | 6.0 | 6.7 |
| Gnome | 7.7 | 8.7 | 7.0 | 7.7 |
| Haga | 9.0 | 7.3 | 7.3 | 8.0 |
| Kenblue | 8.3 | 7.7 | 7.7 | 6.7 |
| Merion | 2.7 | 4.0 | 5.3 | 5.0 |
| Merit | 8.0 | 8.0 | 6.7 | 7.0 |
| Midnight | 8.3 | 7.3 | 5.7 | 6.3 |
| Monopoly | 8.0 | 7.3 | 7.3 | 9.6 |
| Nassau | 7.7 | 8.0 | 7.3 | 8.3 |
| Ram I | 8.7 | 6.7 | 7.0 | 8.3 |
| Victa | 7.7 | 5.7 | 5.7 | 7.3 |
| LSD (.05) | 1.0 | 2.0 | 1.2 | 1.4 |

Rating Scale: 1–9 9 = no disease

TABLE 26

A Comparison of Necrotic Ring Spot Disease Incidence in Ba 69–82 and Other Kentucky Bluegrass Varieties at Post Falls, Id.

| Variety | Necrotic Ring Spot |
|---|---|
| Ba 69–82 | 9.0 |
| Ba 73–540 | 7.3 |
| Abbey | 7.0 |
| Able I | 9.0 |
| Amazon | 6.3 |
| America | 8.3 |
| A-34 | 8.7 |
| Baron | 9.0 |
| Bristol | 8.3 |
| Chateau | 8.0 |
| Classic | 9.0 |
| Coventry | 8.7 |
| Eclipse | 7.7 |
| Estate | 8.3 |
| Georgetown | 9.0 |
| Glade | 9.0 |
| Gnome | 8.3 |
| Haga | 9.0 |
| Kelly | 8.7 |
| Kenblue | 9.0 |
| Merion | 9.0 |
| Merit | 9.0 |
| Midnight | 8.0 |
| Monopoly | 9.0 |
| Mystic | 8.7 |
| Nassau | 9.0 |
| Ram I | 9.0 |
| Victa | 9.0 |
| LSD (.05) | 1.8 |

Rating Scale: 1–9; 9 = no disease

TABLE 27

A Comparison of Red Thread Disease Incidence in Ba 69–82 and Other Kentucky Bluegrass Varieties at Gervais, Oregon

| Variety | % Red Thread |
|---|---|
| Ba 69–82 | 0.0 |

TABLE 27-continued

A Comparison of Red Thread Disease Incidence in Ba 69–82 and Other Kentucky Bluegrass Varieties at Gervais, Oregon

| Variety | % Red Thread |
|---|---|
| Adelphi | 0.0 |
| America | 1.7 |
| Bristol | 0.0 |
| Glade | 15.0 |
| Kenblue | 23.3 |
| Marquis | 6.7 |
| Merit | 6.7 |
| Newport | 3.3 |
| Victa | 10.0 |
| LSD (.05) | 13.0 |

TABLE 28

A Comparison of Percent Drought Damage in Ba 69–82 and Other Kentucky Bluegrass Varieties in Two Annual Tests (A–B) Conducted at Prince Fredrick, Maryland

| | % Drought Damage Test | |
|---|---|---|
| Variety | A | B |
| Ba 69–82 | 0.0 | 17.5 |
| Fylking | 12.5 | 25.0 |
| Kenblue | 5.0 | 7.5 |
| Merion | 2.5 | 15.0 |
| Nugget | 12.5 | 20.0 |
| Newport | 7.5 | 10.0 |
| Vantage | 0.0 | 15.0 |
| Victa | 15.0 | 45.0 |
| LSD (.05) | 11.0 | 29.0 |

TABLE 29

A Comparison of Sod Strength 8 and 12 Months After Planting of Ba 69–82 and Other Kentucky Bluegrass Varities at Remington, VA

| | SOD STRENGTH | |
|---|---|---|
| Variety | 8 Months | 12 Months |
| Ba 69–82 | 26.0 | 20.0 |
| Ba 73–540 | 20.3 | 11.7 |
| Abbey | 17.0 | 8.0 |
| Able I | 16.3 | 8.7 |
| Amazon | 18.0 | 8.7 |
| America | 30.7 | 18.7 |
| A-34 | 21.7 | 9.7 |
| Baron | 25.7 | 14.7 |
| Bristol | 24.7 | 8.3 |
| Challenger | 23.0 | 12.0 |
| Chateau | 23.3 | 15.0 |
| Classic | 23.0 | 15.3 |
| Coventry | 18.0 | 11.0 |
| Eclipse | 22.0 | 13.0 |
| Estate | 23.3 | 16.0 |
| Georgetown | 30.0 | 14.3 |
| Glade | 26.3 | 18.0 |
| Gnome | 22.0 | 14.3 |
| Haga | 22.3 | 13.0 |
| Kenblue | 22.0 | 16.3 |
| Marquis | 23.0 | 12.7 |
| Merion | 21.3 | 11.3 |

TABLE 29-continued

A Comparison of Sod Strength 8 and 12 Months After Planting of Ba 69–82 and Other Kentucky Bluegrass Varities at Remington, VA

| | SOD STRENGTH | |
|---|---|---|
| Variety | 8 Months | 12 Months |
| Merit | 25.3 | 13.3 |
| Midnight | 22.3 | 14.3 |
| Monopoly | 26.0 | 8.3 |
| Nassau | 22.3 | 8.3 |
| Ram I | 22.3 | 11.0 |
| Victa | 29.3 | 16.3 |
| Wabash | 16.7 | 10.3 |
| LSD (.05) | 6.9 | 6.1 |

Rating Scale: Kilograms of tension needed to tear sod.

TABLE 30

Seed Yield Comparison in Pounds Per Acre of Ba 69–82 and Other Kentucky Bluegrass Varieties in Three Annual Tests (A–C) Conducted in Oregon

| | Madras, Oregon | LaGrande, Oregon | |
|---|---|---|---|
| Variety | Test A | Test B | Test C |
| Ba 69–82 | 884 | 920 | 894 |
| Abbey | — | 1253 | 1512 |
| Baron | 1194 | — | — |
| Chateau | 1113 | 857 | 876 |
| Coventry | 1090 | — | — |
| Estate | — | 857 | 876 |
| Marquis | — | 1030 | 1174 |
| Victa | 1324 | 1200 | 1419 |
| LSD | | 181 | 149 |

TABLE 31

A Comparison of Seed Yields in Pounds Per Acre of Ba 69–82 and Other Kentucky Bluegrass Varities at LaGrande, Oregon

| Variety | Yield |
|---|---|
| Ba 69–82 | 1,159 |
| Ba 73–366 | 1,612 |
| Ba 73–381 | 1,551 |
| Ba 74–114 | 748 |
| Abbey | 1,549 |
| Coventry | 1,046 |
| LSD (.05) | 160 |

What is claimed is:

1. A variety of Kentucky bluegrass plant, substantially as shown and described, characterized by a medium to high level of resistance to several serious diseases including leaf spot, melting out, several rusts, dollar spot, powdery mildew and stripe smut, and a desirable green color throughout the growing season, a strong sod former, forms a high quality dense persistent turf under a wide variety of environmental conditions and has a medium level of seed yielding capacity.

* * * * *

UNITED STATES PATENT AND TRADEMARK OFFICE

CERTIFICATE OF CORRECTION

PATENT NO. : Plant 9,611
DATED : July 23, 1996
INVENTOR(S) : Virgil D. Meier

It is certified that error appears in the above-indentified patent and that said Letters Patent is hereby corrected as shown below:

On the title page, item

[75] Add --Eugene W. Mayer-- as co-inventor.

Signed and Sealed this

Seventh Day of January, 1997

*Attest:*

*Attesting Officer*

BRUCE LEHMAN

*Commissioner of Patents and Trademarks*